United States Patent
Glossop

(12) United States Patent (10) Patent No.: US 6,694,164 B2
Glossop (45) Date of Patent: *Feb. 17, 2004

(54) METHOD AND SYSTEM TO IMPROVE PROJECTED IMAGES DURING IMAGE GUIDED SURGERY

(76) Inventor: Neil David Glossop, 44 St. Joseph Street, Suite 806, Toronto, Ontario (CA), M4Y 2W4

( * ) Notice: Subject to any disclaimer, the term of this patent is extended or adjusted under 35 U.S.C. 154(b) by 9 days.

This patent is subject to a terminal disclaimer.

(21) Appl. No.: 09/972,853

(22) Filed: Oct. 10, 2001

(65) Prior Publication Data

US 2002/0016541 A1 Feb. 7, 2002

Related U.S. Application Data

(63) Continuation-in-part of application No. 09/396,472, filed on Sep. 15, 1999, now Pat. No. 6,317,616.

(51) Int. Cl.[7] .................................................. A61B 5/05
(52) U.S. Cl. ........................................ 600/407; 606/130
(58) Field of Search ................... 600/407, 429, 600/426, 427; 606/130; 356/248, 247, 254; 378/206; 382/128; 128/903

(56) References Cited

U.S. PATENT DOCUMENTS 6,317,616 B1 * 11/2001 Glossop ...................... 600/407

* cited by examiner

Primary Examiner—Dennis Ruhl
Assistant Examiner—Runa Shih Qaderi

(57) ABSTRACT

A method and system to facilitate image guided surgery by projecting onto the patient an image corresponding to markings made on pre-acquired images of the patient is disclosed. The image is projected by an imaging projecting device such as a laser which emits coherent visible light. The position of the patient and the image are determined in the same frame of reference. The markings made on the pre-acquired images are then mapped onto the corresponding locations of the patient. The image projecting device then projects images onto the patient corresponding to the markings made on the pre-acquired images. The image is projected substantially normal to a surface of the corresponding locations on the anatomical body to decrease errors arising from the image being optically distorted by the surface features of the patient. The images projected by the image projecting device can be marked onto the patient so that they are visible after the image projecting device stops emitting radiation. Use of a photodynamic substance can also be used in conjunction with the light emitted from the laser to treat tumors and other abnormalities in the patient.

39 Claims, 8 Drawing Sheets

FIG. 6B IMAGE AT POINT A BY PROJECTOR AT POSITION 1

FIG. 6C IMAGE AT POINT A BY PROJECTOR AT POSITION 2

METHOD AND SYSTEM TO IMPROVE PROJECTED IMAGES DURING IMAGE GUIDED SURGERY

RELATED APPLICATION

This application is a continuation-in-part of U.S. application Ser. No. 09/396,472 filed Sep. 15, 1999 now U.S. Pat. No. 6,317,616 and entitled "Method and System to Facilitate Image Guided Surgery".

FIELD OF THE INVENTION

This invention relates generally to image guided surgery. More specifically, the present invention relates to a method and system which facilitates use of pre-acquired images of an anatomical body to pre-plan and perform medical procedures.

BACKGROUND OF THE INVENTION

In recent years, image guided surgery has become more and more common, in part because of the ability of a surgeon to view internal images of a patient's anatomy and pre-plan a medical operation. In this way, pre-acquired images of the anatomical body are used to plan the course of the medical procedure, whether the medical procedure is diagnostic, therapeutic or surgical in nature. The pre-acquired images can also be used, to some extent, during the medical procedure for orientation of the surgeon with respect to the internal anatomy of the patient.

The images of a patient's external or internal anatomy used in image guided surgery can be generated by a number of means, including computerized tomography (CT), magnetic resonance imaging (MRI), video, ultrasound and X-rays. Images may also be captured using angiography, single photon emission computer tomography and positron emission tomography (PET). In all cases, at least two, and generally more than two, images of the patient's internal anatomy are generated. The images are captured such that the relative position of the images is known. The images, along with information indicating the relative position of the images, can then be stored in a data-base to essentially create a data-base body comprised of the pre-acquired images and corresponding to the anatomical body of the patient at the time the images were captured.

This data-base body of images can be used for a number of purposes, including diagnosis or to pre-plan the medical procedure. In addition, it is known in the art to process this data-base body of pre-acquired images in order to produce images of various views, as well as three-dimensional images, based on the relative spatial relationship of the pre-acquired images within the internal anatomical structure of the patient.

Surgeons can pre-plan the course of a medical procedure by marking, either manually or electronically, on the data-base body of pre-acquired images the course of the medical procedure. The markings can indicate areas of interest, objects of concern, as well as proposed cuts or drilling locations and orientations, and locations which must be irradiated with specific types of radiation for diagnostic or therapeutic procedures. During the medical procedure, the surgeon can then refer to the markings on the images to assist in performing the procedure.

Furthermore, the prior art imaging devices can project a representation of the instrument or tool being used by the surgeon onto the pre-acquired images during a medical procedure. The representation corresponds to the position of the actual instrument or tool with respect to the patient. By viewing the position of the representation of the instrument or tool with respect to the data-base body of pre-acquired images, the surgeon can extrapolate the position of the actual probe or instrument with respect to the internal anatomy of the patient. In addition, the surgeon can simultaneously follow the pre-planned markings on the pre-acquired images.

However, the prior art imaging devices and methods suffer from the disadvantage that the surgeon's attention is no longer directed solely toward the patient during the surgery, but rather is also directed toward the pre-acquired images, the pre-planned markings and the representations of the probes and instruments on the images. In other words, during image guided surgery, the surgeon's attention is split between the patient and the data-base image of the patient. This is often disconcerting for surgeons, and in particular surgeons who are unfamiliar with image guided surgery, because their attention is no longer solely directed toward the patient, as is the case with other types of surgery. Rather, the surgeons must view the image of the patient and the representation of the probes and instruments with respect to the data-base image while manipulating the actual probes and instruments within the patient. This can adversely affect the surgeon's hand-eye coordination and could result in the surgeon becoming disoriented.

Also, because the attention of surgeons during image guided surgery is split between the patient and the image of the patient, there is a risk that a surgeon will not notice that the surgeon has stuck, or will strike, a "critical structure" within the patient. Critical structures include an organ or blood vessel, which, if struck, can critically or severely damage the patient. This is compounded by the fact that several imaging techniques do not provide detailed images of critical structures, such as organs or blood vessels, and a surgeon may not immediately see them if the surgeon's attention is directed towards the pre-acquired images rather than at the patient.

A further disadvantage of the prior art imaging systems is that all pre-planned markings made by the surgeon are located on the pre-acquired images. Accordingly, in order to use the pre-planned markings, the surgeon must constantly refer to the images and orient the images and pre-planned markings to the anatomical body during the course of the medical procedure.

SUMMARY OF THE INVENTION

Accordingly, it is an object of this invention to at least partially overcome the disadvantages of the prior art. Also, it is an object of this invention to provide a method and system to facilitate image guided surgery by projecting onto the anatomical body during the medical procedure any markings made onto the data-base body of pre-acquired images.

Accordingly, in one of its aspects, this invention resides in a system for projecting onto an anatomical body markings made on a data-base body of pre-acquired images of the anatomical body, said system comprising: a spatial determinator for determining spatial positional information of the anatomical body in a frame of reference and generating first positional signals indicative of the spatial positional information of the anatomical body in the frame of reference; a mapping unit for receiving first positional signals indicative of the spatial positional information of the anatomical body in the frame of reference, mapping the markings made on the data-base body of pre-acquired images onto corresponding locations on the anatomical body and generating a mapping signal indicative of the corresponding locations in the frame of reference of the markings on the data-base body; and an image projecting device for receiving the mapping signal and projecting an image of the markings made on the data-base body onto the corresponding locations of the anatomical body.

In a still further aspect, the present invention provides a system for projecting onto an anatomical body markings made on a data-base body of pre-acquired images of the anatomical body, said system comprising: a spatial determinator for determining spatial positional information of the anatomical body by tracking the anatomical body in a frame of reference and generating first positional signals indicative of the spatial positional information of the anatomical body in the frame of reference; a mapping unit for receiving first positional signals indicative of the spatial positional information of the anatomical body in the frame of reference, mapping the markings made on the data-base body of pre-acquired images onto corresponding locations on the anatomical body and generating a mapping signal indicative of the corresponding locations in the frame of reference of the markings on the data-base body; and an image projecting device for receiving the mapping signal and projecting an image of the markings made on the data-base body onto the corresponding locations of the anatomical body, said image projecting device projecting the image substantially normal to a surface of a portion of the corresponding locations of the anatomical body.

In a further aspect, the present invention resides in a method for projecting onto an anatomical body markings made on a data-base body of pre-acquired images of the anatomical body, said method comprising the steps of: obtaining spatial positional information of the anatomical body in a frame of reference; mapping the markings made on the data-base body of pre-acquired images onto the corresponding locations on the anatomical body; and projecting an image of the markings made on the data-base body onto the corresponding locations of the anatomical body in the frame of reference.

In a further aspect, the present invention provides a method for projecting onto an anatomical body markings made on a data-base body of pre-acquired images of the anatomical body, said method comprising the steps of: obtaining spatial positional information of the anatomical body by tracking the anatomical body in a frame of reference; mapping the markings made on the data-base body of pre-acquired images onto corresponding locations on the anatomical body; and projecting an image of the markings made on the data-base body onto the corresponding locations on the anatomical body in the frame of reference substantially normal to a surface of a portion of the corresponding locations of the anatomical body.

One of the advantages of the present invention is that an image corresponding to the markings made by the surgeon onto the data-base body of pre-acquired images can be viewed during the surgical procedure directly on the patient. In other words, the surgeon will have the benefit of any markings made on the pre-acquired images during pre-planning of the medical procedure while the surgeon's attention is directed to the patient. This permits the surgeon to more easily perform the medical procedure in a manner that the surgeon is accustomed to, rather than by watching the pre-acquired images and a representation of the instruments on the images.

A further advantage of the present invention is that the attention of the surgeon will be directed towards the patient for greater periods of time during the medical procedure. This will assist in the surgeon identifying critical structures, which may or may not have appeared in the pre-acquired images, before they are struck. Also, even if the critical structures have appeared on the pre-acquired images, the internal anatomy of the patient may have changed since the pre-acquired images were captured. For example, the internal organs or veins of a patient could have moved, either by movement of the patient, the actual incision by the surgeon, or other means. Clearly, these movements will not be reflected in the pre-acquired images as the movements occurred after the pre-acquired images were captured and the surgeon will only notice the changes by viewing the patient.

Another advantage of the present invention is that a surgical procedure can be planned by a surgeon located remote from the patient, and, with only the benefit of the pre-acquired images. For instance, the markings made on the pre-acquired images by the surgeon at the remote location will be projected onto the patient to assist the surgeon located proximate to the patient in performing the medical procedure. In addition, both surgeons can continue to mark the pre-acquired images in order to mutually identify the organs in the patient and the corresponding images of the organs in the pre-acquired images. In this way, telesurgery can be facilitated. Furthermore, in a preferred embodiment, the remote surgeon could initially mark portions of the anatomical body with a beam which is only visible to the remote surgeon and not visible to the local surgeon. For instance, the remote surgeon could mark the pre-acquired images to identify organs in the patient with an infrared laser. The infrared laser may be visible to a remote surgeon if the camera used by the remote surgeon can see infrared beams. However, the infrared beam would not be visible to the local surgeon. This may be advantageous by allowing the remote surgeon to take a moment and carefully draw and/or edit a region of interest entirely "in private" before projecting an image to the local surgeon using visible light which the local surgeon can see. In this way, the local surgeon is not distracted while the remote surgeon becomes satisfied with the markings which one surgeon desires to show to the local surgeon. This technique can also be used for teaching purposes, or any other purpose in which the remote surgeon desires to mark specific areas which can only be seen by one surgeon and not the other surgeons.

Another advantage of the present invention is that the images projected by the image projecting device can be marked, either temporarily or permanently, onto the patient. This can be performed by having an image projecting device which emits radiation that can permanently mark a patient, such as by use of a $CO_2$ laser which could mark the image onto the anatomy of the patient, either on the skin or on the bone. In a similar manner, use of an ultraviolet laser could be used to leave a mark on the skin of the patient corresponding to markings made to the pre-acquired images. Likewise, use of a photoreactive ink which perceptively changes in response to radiation emitted by the image projecting device can be used to temporarily mark the patient with markings made to the pre-acquired images. In a preferred embodiment, the photoreactive ink may be either thermochromic ink, which reacts to infrared radiation, or, photochromic ink which can react to different types of radiation, such as ultraviolet radiation. More preferably, the photoreactive ink may be embedded in a material, such as plastic, which is draped over the patient and then marked with the radiation emitted by the image projecting device, rather than applying the substance to the surface of the patient. In this way, the photoreactive ink embedded in the marking material would perceptively change and the image appear on the marking material, rather than the image appearing on a substance applied to the patient. In either case, a surgeon can quickly and accurately mark onto the patient any markings made onto the images during pre-planning, such that the markings will appear on the anatomical body after the image projecting device ceases projecting the image.

In another aspect of the present invention, the markings on the pre-acquired images can correspond to areas or tumors which must be irradiated as part of a photodynamic therapeutic procedure. In other words, substances which can change cells of the patient, such as photodynamic agents which react to specific types of radiation to become cytotoxic, can be applied to the patient. The image projecting device can be programmed to emit the types of radiation to which the photodynamic agent reacts. In this way, portions of the patient, such as tumors, can be eliminated or destroyed in a precise and predetermined manner by irradiating the patient with the specific type of radiation in a pre-planned manner. Also, because the radiation will be applied in a specific and pre-planned manner, a higher level of accuracy can be obtained for irradiating the patient, and therefore a more general photodynamic agent can be used which may be partially absorbed by the healthy tissue, as only the tumors will be irradiated. Likewise, a more intense beam of light can be used because it is less likely that healthy tissues will be irradiated.

Another advantage of the present invention is that the image projecting device can emit radiation to cauterize an area of the body. In this way, the area of the patient which is to be cauterized, such as the portion of the brain around a tumor that is to be removed, can be pre-planned and executed automatically once the tumor has been removed.

In a further embodiment, the image is projected substantially normal to a surface of the corresponding locations or a portion of the corresponding locations. In this way, by projecting the image substantially normal to a surface of the corresponding locations of the anatomical body, a clearer image is produced and optical distortions are reduced. Preferably, the image projecting device projects the image within 45 degrees of the normal of the surface where the corresponding locations are located. More preferably, the image projecting device projects the image within 30 degrees of the normal of the surface where the corresponding locations are located. If the corresponding locations extend over a large surface of the patient such that it is not possible to have a single image projecting device which can project an image substantially normal to the surface having the corresponding locations, the image projecting device may comprise more than one emitter such that different portions of the image will be projected by different emitters, each emitter projecting its portion of the image substantially normal to a part of the surface where the corresponding locations are located. In the event where two emitters are not practical, or, an entire image can still not be projected substantially normal to the entire surface where the corresponding locations are located, the portion of the image which is not substantially normal to a surface can be projected in a different manner, such as with dashed lines or in a different color, to bring to the attention of the surgeon that part of the image may contain optical distortion errors due in part to the image not being projected normal to the surface of the patient, or by surface features of the patient.

In a further embodiment, the image projecting device is then moved to a location which optimally projects the image onto the anatomical body. This position is generally determined to be a position whereby the projected beam is incident substantially normal to the surface upon which the image is being projected. Preferably, the incident angle is within 45 degrees, and more preferably 30 degrees, of the normal of the surface. To facilitate this, preferably the position and orientation of the image projecting device is tracked in the frame of reference. In this way, optical distortion errors have been found to be decreased, thereby improving their overall image projected by the image projecting device.

Further aspects of the invention will become apparent upon reading the following detailed description and drawings which illustrate the invention and preferred embodiments of the invention.

BRIEF DESCRIPTION OF THE DRAWINGS

In the drawings, which illustrate embodiments of the invention:

FIGS. 6B and 6C illustrate the projected image from the two different positions shown in FIG. 6A;

DETAILED DESCRIPTION OF THE PREFERRED EMBODIMENTS

Figure 1:
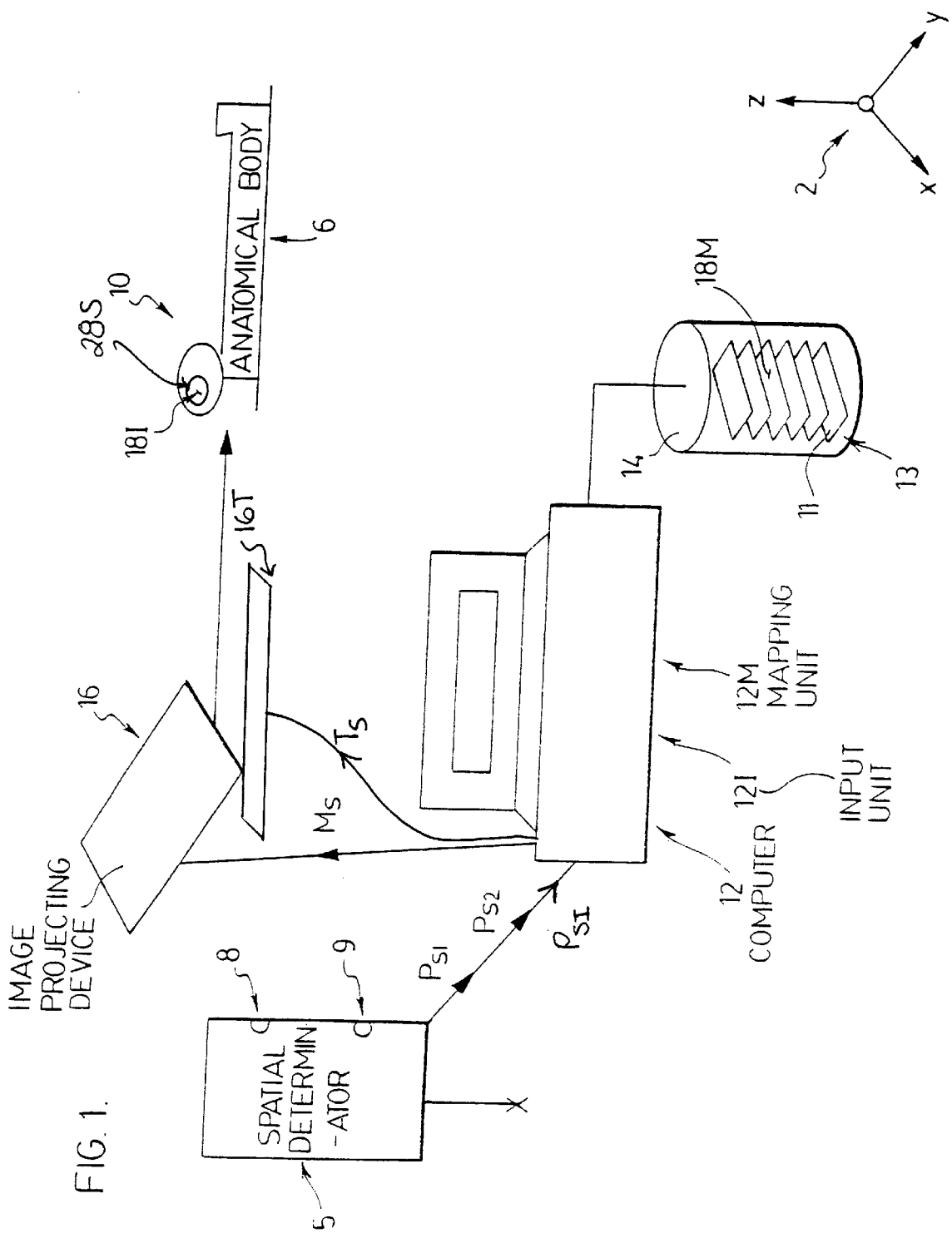
FIG. 1 shows a symbolic representation of a system according to one embodiment of the present invention.

FIG. 1 illustrates the system, shown generally by reference numeral 10, according to one embodiment of the present invention. As shown in FIG. 1, the system 10 comprises a spatial determinator 5 which can determine spatial positional information for various objects in the frame of reference 2. The frame of reference 2, which is shown symbolically by the xyz origin, is generally the frame of reference 2 within which the patient 6 is located.

The spatial determinator 5 can be any type of device which can determine the spatial position of objects in the frame of reference 2. However, in a preferred embodiment, the spatial determinator 5 comprises an optical tracking system which utilizes two cameras 8 and 9 to track the position and orientation of objects in the frame of reference 2 and send position signals $P_S$ indicative of the spatial positional information of the objects being tracked in the frame of reference 2. It is understood that the spatial positional information may include information regarding the position, as well as the orientation, of the object in the frame of reference 2.

One object which the spatial determinator 5 tracks in the frame of reference 2 is an anatomical body which, in the embodiment shown in FIG. 1, corresponds to the patient 6. The spatial determinator 5 will determine the spatial position of the patient 6 and generate first positional signals $P_{S1}$ indicative of the spatial positional information of the anatomical body 6 in the frame of reference 2.

The first positional signals $P_{S1}$ are received by a mapping unit 12M which, in the embodiment shown in the FIG. 1, is contained in a computer 12. It is understood that the mapping unit 12M can be contained within any physical structure which can execute the functions of the mapping unit 12M and the computer 12 shown in FIG. 1 is simply presented as a representation of one possible physical structure within which the mapping unit 12M may be contained.

The mapping unit 12M is connected to a storage unit 14 within which pre-acquired images 11 of the anatomical body 6 are stored. The pre-acquired images 11 stored within the storage unit 14 can form a data-base body 13 of the patient 6, as is known in the art. The storage unit 14 can comprise any type of storage medium to store the data-base body 13 of pre-acquired images 11 for use by the mapping unit 12M.

In addition to the data-base body 13 of pre-acquired images 11, the storage unit 14 will also have stored thereon any markings, shown generally by reference numeral 18M, made on the data-base body 13. In other words, if a surgeon or other person has made markings 18M on the data-base body 13, these markings will be stored in the storage unit 14 and can be accessed by the mapping unit 12M. The markings 18M may be stored either with the images 11 or separately with an indication of how the markings 18M relate to the data-base body 13 of pre-acquired images 11.

The mapping unit 12M receives the first positional signal $P_{S1}$ from the spatial determinator 5 indicating the spatial positional information of the anatomical body 6 in the frame of reference 2. The mapping unit 12M then maps the markings 18M made on the data-base body 13 of pre-acquired images 11 onto corresponding locations of the anatomical body 6. In order to accomplish this, a registration procedure, as is known in the art, will generally be performed to register key features on the anatomical body 6 to corresponding key features on the data-base body 13.

In a further preferred embodiment, a compensation procedure can be performed. The compensation procedure follows the initial registration procedure. In the compensation procedure, a control point is selected in the frame of reference 2. Preferably, the control point is on or near the anatomical body 6. The image projecting device 16 then projects an image onto the control point. The position that is illuminated is then determined using the spatial determinator 5. The difference between the control point and the point illuminated by the laser is then determined. This difference is recorded as an error that is used to correct any systematic errors, such as numerical round-off errors, which may be present in the system. This difference can then be used as a compensation value which can be included in the system to compensate for the numerical or systematic errors.

The mapping unit 12M will then generate a mapping signal $M_S$ indicative of the corresponding locations in the frame of reference 2 of the markings 18M made on the data-base body 13. In other words, the mapping signal $M_S$ will comprise the xyz positional information of the corresponding locations in the frame of reference 2, and likely on the anatomical body 6, of the markings 18M made on the data-base body 13. In cases where the orientation of the markings 18M is relevant, the mapping signal $M_S$ will also comprise the information regarding the orientation of the markings 18M in the frame of reference 2. The mapping signal $M_S$ is then received by an image projecting device 16. The image projecting device 16 can comprise a laser or other image projecting device 16 which can project an image onto any position in the frame of reference 2.

The image projecting device 16 projects an image, shown generally by reference numeral 18I, based on the mapping signal $M_S$. The image 18I corresponds to the markings 18M made on the data-base body 13, but projected onto the corresponding locations of the anatomical body 6 in the frame of reference 2. For example, if a surgeon had marked the pre-acquired images 11 with a marking 18M indicating the incision to be made, the image 18I will correspond to the location on the anatomical body 6 where the marking 18M for the incision was made on the data-base body 13.

In a preferred embodiment, the image projecting device 16 projects the image 18I in a manner which can be tracked by the spatial determinator 5. In this way, the spatial determinator 5 can track the image 18I and determine the spatial information for the image 18I in the frame of reference 2. The spatial determinator 5 can then generate a second positional signal $P_{S2}$ indicative of the spatial positional information of the image 18I in the frame of reference 2. The mapping unit 12M receives the second positional signal $P_{S2}$ in addition to the first positional signal $P_{S1}$ and can determine whether or not the image 18I being projected by the image projecting device 16 corresponds to the position of the markings 18M made on the data-base body 13 of pre-acquired images 11. If the mapping unit 12M detects a disparity between the actual location of the image 18I being projected and the intended location of the projection, the mapping unit 12M can send a modified mapping signal $M_S$ to correct the disparity and project a more accurate image 18I.

Preferably, the image projecting device 16 can project the image by emitting radiation which is perceptible by the spatial determinator 5. For example, if the spatial determinator 5 comprises an optical tracking system having cameras 8 and 9, the cameras 8 and 9 can sense or perceive the radiation being emitted by the image projecting device 16, and thereby generate the second positional signal $P_{S2}$ indicative of the spatial positional information of the image 18I in the frame of reference 2. If the cameras 8 and 9 of the optical tracking system cannot track visible radiation, it will be necessary for the image projecting device 16 to first project the image 18 by emitting radiation which is perceptible to the cameras 8, 9. Once the mapping unit 12M has determined that the image 18I being projected corresponds to the markings 18M made on the data-base body, the projecting device 16 will then emit radiation which is visually perceptible. In a further embodiment, the projecting device 16 will emit radiation which marks the image 18I onto the anatomical body 6 such that the markings appear on the anatomical body after the image projecting device ceases projecting the image.

In a further preferred embodiment, to ensure that the image 18I appears correctly at the corresponding location, it is preferred that the image projecting device 16 projects the image 18I substantially normal to a surface 28S of a portion of the corresponding locations of the anatomical body 6. In this way, optical distortion errors can be decreased. Furthermore, for images 18I projected after an incision has been made, it is less likely that another object, such as a part of the anatomical body 6, interferes with the projection of the image 18I. Preferably, the image 18I is projected within 45 degrees, and more preferably within 30 degrees, of the normal of the surface 28S having a portion of the corresponding locations.

In order to project the image 18I substantially normal to the surface 28S of the portion of the corresponding locations, it is generally necessary to orient the image projecting device 16 with respect to the anatomical body 6 such that the image 18I can be projected substantially normal to the surface 28S. This can be accomplished by either moving the anatomical body 6 or moving the image projecting device 16.

In a preferred embodiment, the system 10 comprises translation device 16T shown symbolically in FIG. 1. The translation device 16T receives translation signals $T_S$, generally from the mapping unit 12M, or another unit designed to generate the translation signals $T_S$, to move the image projecting device 16 to a position and orientation such that the image projecting device 16 projects the image 18I substantially normal to the surface 28S of the portion of the corresponding locations. In order to accomplish this, it is also generally necessary for the mapping unit 12M to know the position of the image projecting device 16 in the frame of reference 2. In one embodiment, this can be accomplished by the translation device 16T monitoring how the image projecting device 16 is moved, such as by using stepper motors or an encoder. Alternatively, the spatial determinator 5 can track the movement of the image projecting device 16 in the frame of reference 2 and generate image projecting position signals $P_{SI}$ indicative of the position of the image projecting device 16 in the frame of reference 2. The mapping unit 12M then receives the image projecting position signals $P_{SI}$ and sends the translation signal $T_S$ to the translation device 16T to move the image projecting device 16 to a position and orientation with respect to the anatomical body 6 such that the image projecting device 16 can project the image 18I substantially normal to the surface 28S of the portion of the corresponding locations.

In a preferred embodiment, the normal to the surface 28S are calculated by the mapping unit 12M from the pre-acquired images 11 stored in the storage unit 14, as is known in the art. Preferably, in order to confirm the calculated normals, the image projecting device 16 projects known images, such as triangles, onto the surface 28S prior to the procedure commencing. The known images projected on the surface 28S of the anatomical body 6 can then be monitored to determine if the projected known images appear in a manner consistent with the calculated normals. For instance, when an optical tracking system utilizing cameras 8 and 9 is used for the spatial determinator 5, the cameras 8, 9 can monitor the known images projected on the anatomical body 6. The known images can then be analyzed to determine planes, and normals to these planes. For instance, if triangles are used, the vertices of the triangles are used to form planes from which normals can be calculated. These normals represent the actual normals of the surfaces on the anatomical body 6 and these actual normals are compared to the calculated normals from the database body 13 to ensure they are consistent. If they are not consistent, revised calculations are made and/or now images may be required.

Preferably, the computer 12 also comprises an input unit 12I for inputting information, including instructions and data. For example, the inputting unit 12I can be used to input additional markings 18M onto the data-base body 13. In this way, a surgeon can continuously make markings 18M on the database body 13 during the procedure. The projecting device 16 can then project images 18I of the markings 18M, including the markings made through the input unit 12I, onto the patient 6.

In addition, if several markings 18M are made on the data-base body 13 of pre-acquired images 11, the input unit 12I can be used to input information comprising instructions as to which marking 18M the image projecting device 16 should be projecting. For example, during a surgical procedure, the surgeon may have marked onto the data-base body 13 markings 18M reflecting the incision, the position and orientation of an entry point, as well as internal features of the patient 6 which should be treated. Accordingly, the input unit 12I can be used by the surgeon to input instructions as to which markings 18M should be projected during different stages of the surgical procedure. In addition, if the projecting device 16 can project two different images 18I simultaneously, such as if the projecting device 16 emits a first coherent beam of visible light and a second coherent beam of visible light, the surgeon can use the input unit 12I to select not only which markings 18M are being projected, but also which coherent beam of light is being used to project the corresponding images 18I. This is particularly useful if the image projecting device 16 emits a second coherent beam of visible light which is of a different wavelength, and therefore different colour, than the first coherent beam of visible light, so that the surgeon can easily distinguish between the two images 18I being projected.

It is also understood that the input unit 12I need not be located proximate the computer 12. In other words, a surgeon located remote from the second frame of reference 2 can have an input unit 12I and send information, including instructions as to additional markings 18M and a selection of the markings 18M to be projected to the computer 12. In this way, telesurgery can be facilitated by the surgeon located proximate the patient 6 immediately seeing the projection of the image 18I, the markings 18M being made and selected by a remotely located surgeon. This facilitates image guided surgery by permitting a remotely located surgeon to guide the proximately located surgeon through the procedure by projecting images 18I of the marking 18M made by the remotely located surgeon directly onto the patient 6.

Likewise, if two surgeons are located proximate the patient 6, both surgeons can also use the input unit 12I to non-obtrusively identify portions of the patient's 6 anatomy by marking the portion on the data-base body 13 and then having the image projecting device 16 project the image 18I corresponding to the markings 18M. This could also be used by instructors to identify items of interest in a non-evasive manner by projecting the image 18I onto the items of interest, rather than touching the actual items of interest.

It is understood that the input unit 12I can comprise any type of means for inputting information. For example, the input unit 12I can comprise a keyboard or a mouse. The input unit 12I can also be voice-activated such that a surgeon can send verbal commands to the input unit 12I as to which markings 18M should be projected.

Figure 2:
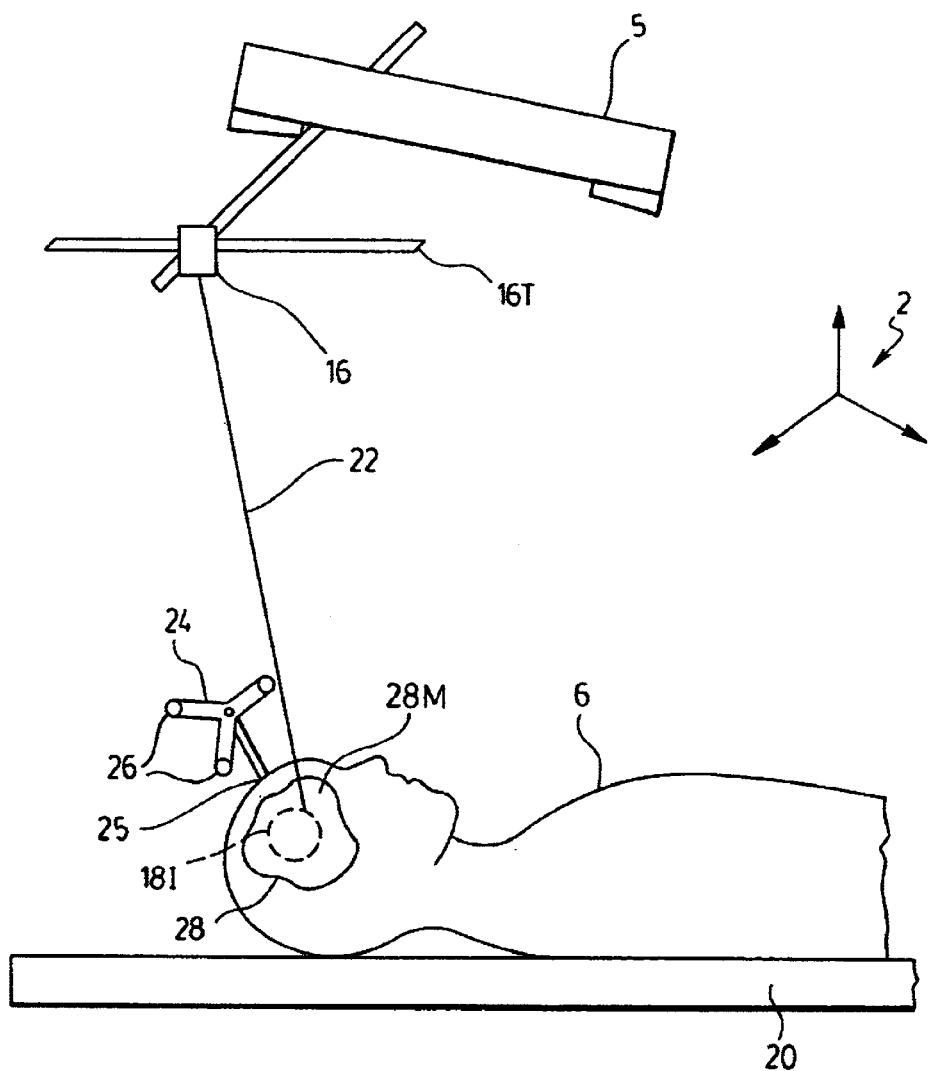
FIG. 2 is a further symbolic representation of a system according to one embodiment of the present invention to project an image.

FIG. 2 shows a further embodiment of the present invention. In FIG. 2, the image projecting device 16 comprises a laser which emits a coherent beam of visible light, such as laser beam 22. It is understood that the image projecting device 16 may be calibrated or otherwise registered so that it could direct the laser beam 22 to a known position in the frame of reference 2 in response to the mapping signals $M_S$. In order to assist in directing the laser beam 22, the system 10 can comprise translation devices 16T which can move the image projecting device 16 such that the laser beam 22 will have the proper position and, if desired, orientation. In a further embodiment, as discussed above, the translation devices 16T move the image projecting device 16 in response to the translation signals $T_S$ to a position and orientation such that the image projecting device 16 projects the image 18I substantially normal to a surface 28S of the portion of the corresponding locations.

In a preferred embodiment, the spatial determinator 5 tracks the position of the image projecting device 16. This may assist in calibrating or registering the image projecting device 16 in the frame of reference 2. Also, if the image projecting device 16 comprises translation devices 16T, the spatial determinator 5 can track the position of the image projecting device 16 and send the image projecting signal $P_{SI}$ to the mapping unit 12M indicative of the position of the image projecting device 16 in the frame of reference 2. The mapping unit 12M can then determine whether or not the image projecting device 16 has been moved by the translation devices 16T to the correct position to project image 18I of the markings 18M made on the data-base body 13 onto the corresponding locations of the anatomical body 6 in the frame of reference 2 and substantially normal to a surface 28S of the portion of the corresponding locations.

As also illustrated in FIG. 2, it is preferred that the spatial determinator 5 be located proximate the image projecting device 16 in the frame of reference 2. In this way, it will be possible for the spatial determinator 5 to easily track the image 18I being produced by the laser beam 22. Also, it is desirable to have the spatial determinator 5 and the image projecting device 16 proximate to each other and out of the way from the surgeons and other medical equipment. In this regard, it is preferable that both the spatial determinator 5 and the image projecting device 16 be located in otherwise unused space, such as near the ceiling of the operating room.

Figure 8:
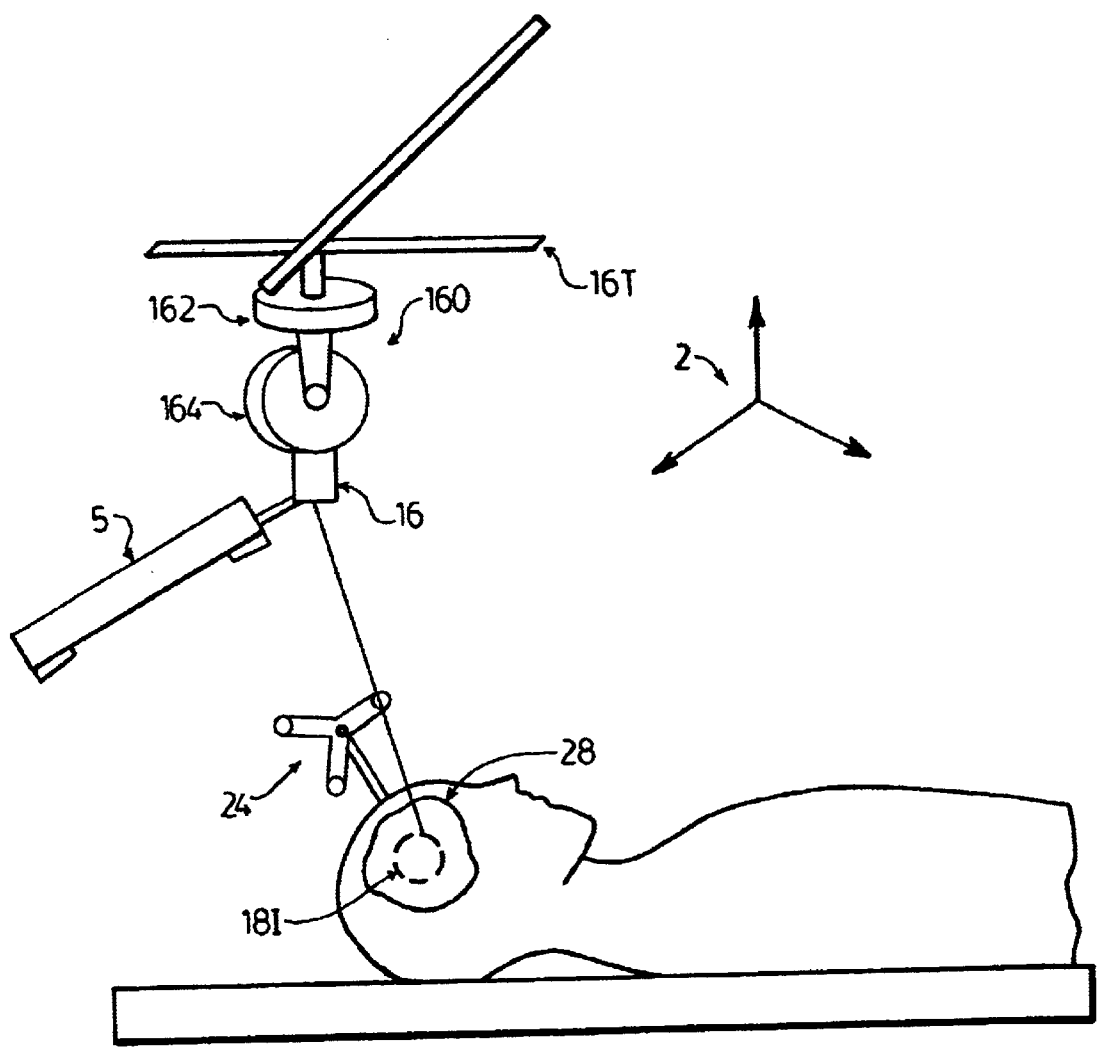
FIG. 8 is a symbolic representation of a further embodiment of the present invention where the spatial determinator moves with the image projecting device.

In a preferred embodiment, as illustrated in FIG. 8, the spatial determinator 5 is associated with the image projecting device 16 such that the image projecting device 16 and the spatial determinator 5 will move together. In this way, the position of the image projecting device 16 need not be explicitly determined by the spatial determinator 5. Rather, the position of the image projecting device 16 in the frame of reference 2 will be the same as the position of the spatial determinator 5 such that the image projecting position signals $P_{SI}$ correspond to the position of the spatial determinator 5 in the frame of reference 2. This is advantageous for several reasons. For instance, to any extent that the image projecting device 16 and spatial determinator 5 move together, their frames of reference will be related. This will increase the accuracy of the overall system by decreasing the transformations between the image projecting device 16 frame of reference and the spatial determinator 5 frame of reference. Furthermore, the volume within which the spatial determinator 5 can track objects is often limited. Therefore, by not tracking the image projecting device 16, which is generally located near the spatial determinator 5, the spatial determinator 5 can track a larger volume around the operating site, including the anatomical body 6 and the images 18I being projected onto the anatomical body 6.

Figure 7:
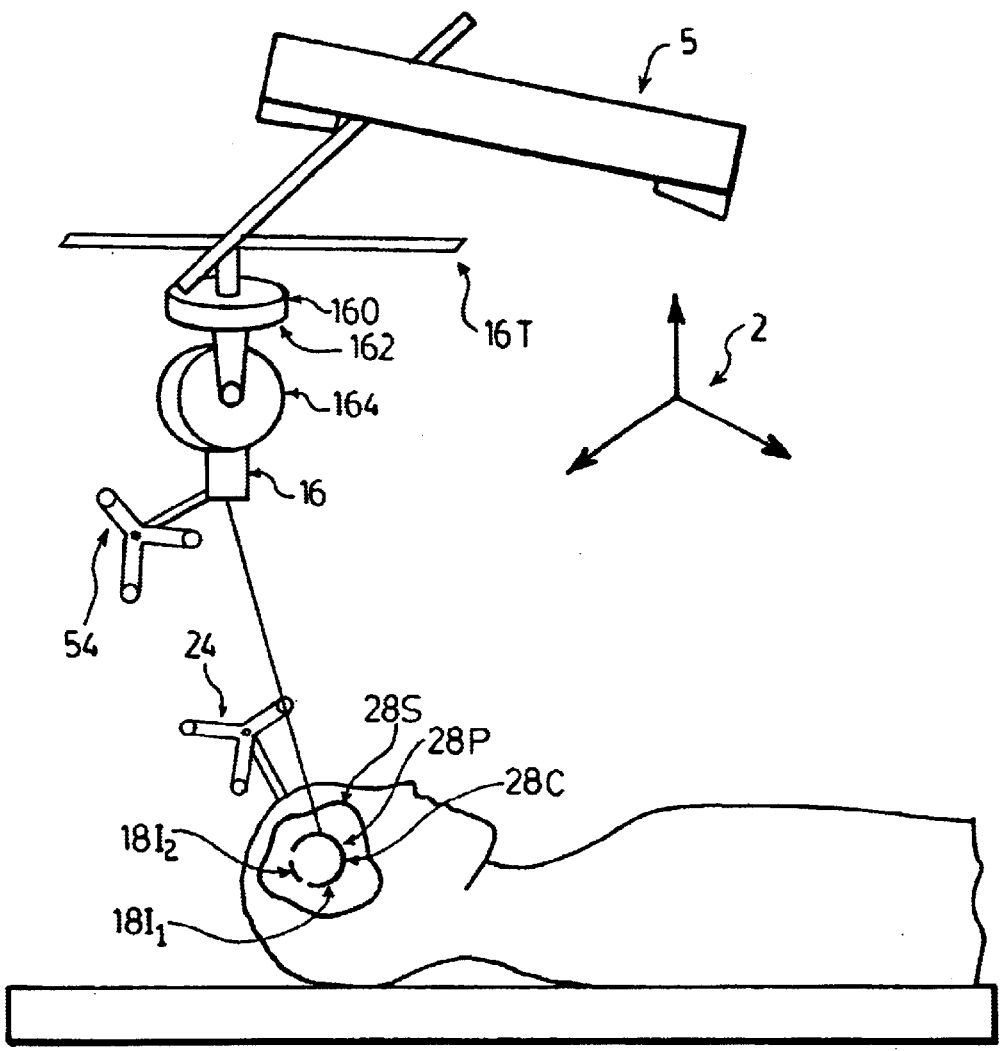
FIG. 7 is a symbolic representation of a system according to a further embodiment of the present invention with a swivel and tilt base unit.

FIG. 8 shows an improved translation device 16T which comprises a swivel/tilt base unit 160 having a pan rotary table 162 and a tilt rotary table 164, which components are described in more detail below with respect to FIG. 7. For present purposes, however, it should be understood that the spatial determinator 5 need not be fixed to the swivel/tilt base unit 160, but rather could be only fixed or associated with the translation portion of the translation device 16T. In this embodiment, not shown in FIG. 8, the spatial determinator 5 would be moved within the image projecting device 16 in the frame of reference 2, but would not be rotated by the swivel/tilt base unit 160 with the image projecting device 16. This is particularly advantageous where the spatial determinator 5 is bulky or heavy and cannot be easily moved by the swivel/tilt base unit 160, but can be moved by the translation portion of the translation device 16T.

The patient 6, also referred to as the anatomical body, in FIG. 2 is positioned on a table, such as an operating table 20. As shown in FIG. 2, the image projecting device 16 will project the image 18I onto the patient 6.

If the image 18I comprises a circle or other two-dimensional representation, the image projecting device 16 can quickly move the laser beam 22 to produce the image 18I. The laser beam 22 can be moved rapidly by the image projecting device 16 so that the viewer will perceive a substantially continuous image 18, represented by the dotted line on the patient 6 in FIG. 2, by the persistence of vision effect. The image projecting device 16 will generally comprise a pair of mirrors which can move quickly to produce the image 18I. If desired, fluorescence or other methods could also be used. It is understood that as the surface upon which the image 18I will be projected will be the surface of an anatomical feature of the patient 6, and therefore not necessarily flat. The projecting device 16 and the mapping unit 12M will compensate for the shape of the anatomical feature of the patient 6 so that image 18I of the markings 18M made on the data-base body 13 appear on the corresponding locations of the anatomical body of the patient 6 even though the surface is not flat, and, projecting the image 18I substantially normal to a surface 28S containing the corresponding locations of the anatomical body 6. If it is not possible to project the image 18I substantially normal to the entire surface 28S, the image projecting device 16 will attempt to project the image 18I normal to the surface 28S of at least a portion of the corresponding locations.

It is understood that the image 18I can be any type of two dimensional representation. For instance, in one embodiment as described above, the image projecting device 16 could be produced by one or more coherent beams which can move over the surface 28S to create the image 18I. In this case, preferably, the angle of incidence of the one or more coherent beams are substantially normal to the surface 28S of at least a portion of the corresponding locations as the beam is scanned over the surface 28S to produce the image 18I. This is described in more detail below with respect to FIGS. 6A, 6B and 6C. The image 18I could also be a fixed image generated from a slide or computer generation techniques. In this case, the image 18I would be preferably projected such that the image 18I is substantially normal to the surface of at least a portion of the corresponding locations.

In addition, the laser beam 22 could be configured such that it can mark the image 18I onto the patient 6. This can be accomplished, for example, by using an image projecting device 16 which emits a laser beam 22 that can mark the patient 6 with the image 18I such that the image 18I will appear even after the laser beam 22 is no longer emitting radiation. For example, use of a projecting device 16 which comprises a $CO_2$ or ultraviolet laser could mark the image 18I onto the anatomy, such as either on the skin or on the bone, of the patient 6. In this way, once the image 18I has been temporarily or permanently marked on the patient 6, the image projecting device 16 can then cease projecting the image 18I and discontinue emitting the laser beam 22.

In a preferred embodiment, use of photoreactive ink, shown generally by reference numeral 28 in FIG. 2, can be applied to the patient 6. The photoreactive ink 28 would preferably react to the radiation emitted by the image projecting device 16, such as the laser beam 22, and change in a visually perceptible manner in response to the laser beam 22. The image projecting device 16 can be designed to emit radiation of different wavelengths so that one wavelength can be visually perceived and the other wavelength can cause the substance to perceptively change. In this way, the image 18I projected by the image projecting device 16 would be temporarily or permanently marked onto the patient 6 by means of the photoreactive ink perceptively changing in response to the emitted radiation. Accordingly, in this way, the markings 18M made on the data-base body 13 can be easily transferred to temporary or permanent markings on the patient 6 by means of the projected image 18I. In this case, it is understood that radiation emitted by the image projecting device 16 need not be visually perceptible, but only cause the photoreactive ink 28 to react in a perceptible manner. Alternatively, in a further preferred embodiment, the photoreactive ink 28 is not placed directly on the patient 6, but rather is embedded in a marking material, shown generally by reference numeral 28M in FIG. 2. The marking material 28M can be applied to the anatomical body 6 such that projecting the image 18I in a type of radiation to which the substance 28 reacts onto the marking material 28M will mark the marking material on the anatomical body 6 with the image 18I projected by the image projecting device 16. In this way, the image 18I can be marked indirectly on the patient 6 by marking the image 18I on the marking material 28M.

It is understood that any type of photoreactive substance 28 can be used either directly on the patient 6, or, embedded in the marking material 28M. Preferably, the photoreactive ink 28 will react to a type of radiation which is not present ordinarily in the operating room, either in terms of wavelength, intensity or characteristics. For example, the photoreactive ink 28 could react to infrared radiation or ultraviolet radiation, which are not generally present in the operating room in intensities sufficient to cause the photoreactive ink 28 to otherwise react in a perceptible manner. Radiation of various other wavelengths could also be used. In other applications, x-ray radiation or even particle beams, could be used to cause the substance 28 to react in a perceptible manner.

FIG. 2 also shows a tracking tool 24 attached to the patient 6 by means of a support 25. The tracking tool 24 can assist in tracking the position and orientation of the patient 6 in the frame of reference 2. In a preferred embodiment, where the spatial determinator 5 comprises an optical tracking system having cameras 8 and 9, the tracking tool 24 will have tracking emitters or reflectors 26 which can be perceived by the cameras 8, 9. In this way, the cameras 8, 9 can easily track the position of the tracking elements 26 and thereby determine the position and orientation of the patient 6 in the frame of reference 2. The tracking tool 24 can comprise any type of tracking tool, such as the tracking tool described in U.S. Pat. No. 5,834,759 which is incorporated herein by reference.

Figure 5:
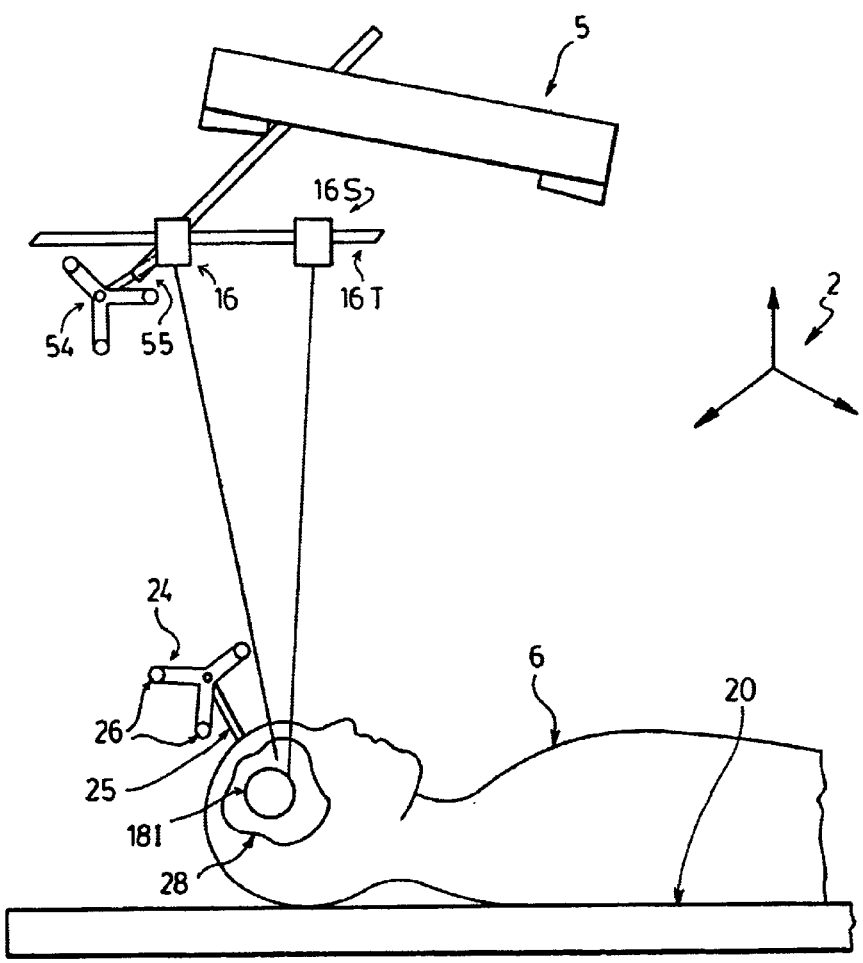
FIG. 5 is a symbolic representation of a system according to a further embodiment of the present invention which tracks the position of the image projecting device.

In a further preferred embodiment as illustrated in FIG. 5, a tracking tool 54, similar to the tracking tool 24, is attached to the image projecting device. The tracking tool 54 is attached to the image projecting device 16 by support 55. The tracking tool 54 has tracking elements 26 which, in a preferred embodiment, can be easily tracked by the cameras 8, 9. This facilitates tracking the position and orientation of the image projecting device 16 in the frame of reference by the spatial determinator 5. The spatial determinator 5 can then send the image projecting signal $P_{SI}$ to the mapping unit 12M. In this way, the mapping unit 12M can determine the position of the image projecting device 16, and, whether or not the image projecting device 16 has been moved by the translation device 16T to the correct position. In an alternate embodiment, the translation device 16T comprises a stepper motor or encoder which accurately monitors its movement and the movement of the image projecting device 16. The position of the image projecting device 16 in the frame of reference 2 can then be determined by signals $P_{SI}$ from the step promoter or encoder. In either case, the mapping unit 12M will receive position signals $P_{SI}$ indicative of the position of the imaging projecting device 16 in the frame of reference 2.

Figure 3:
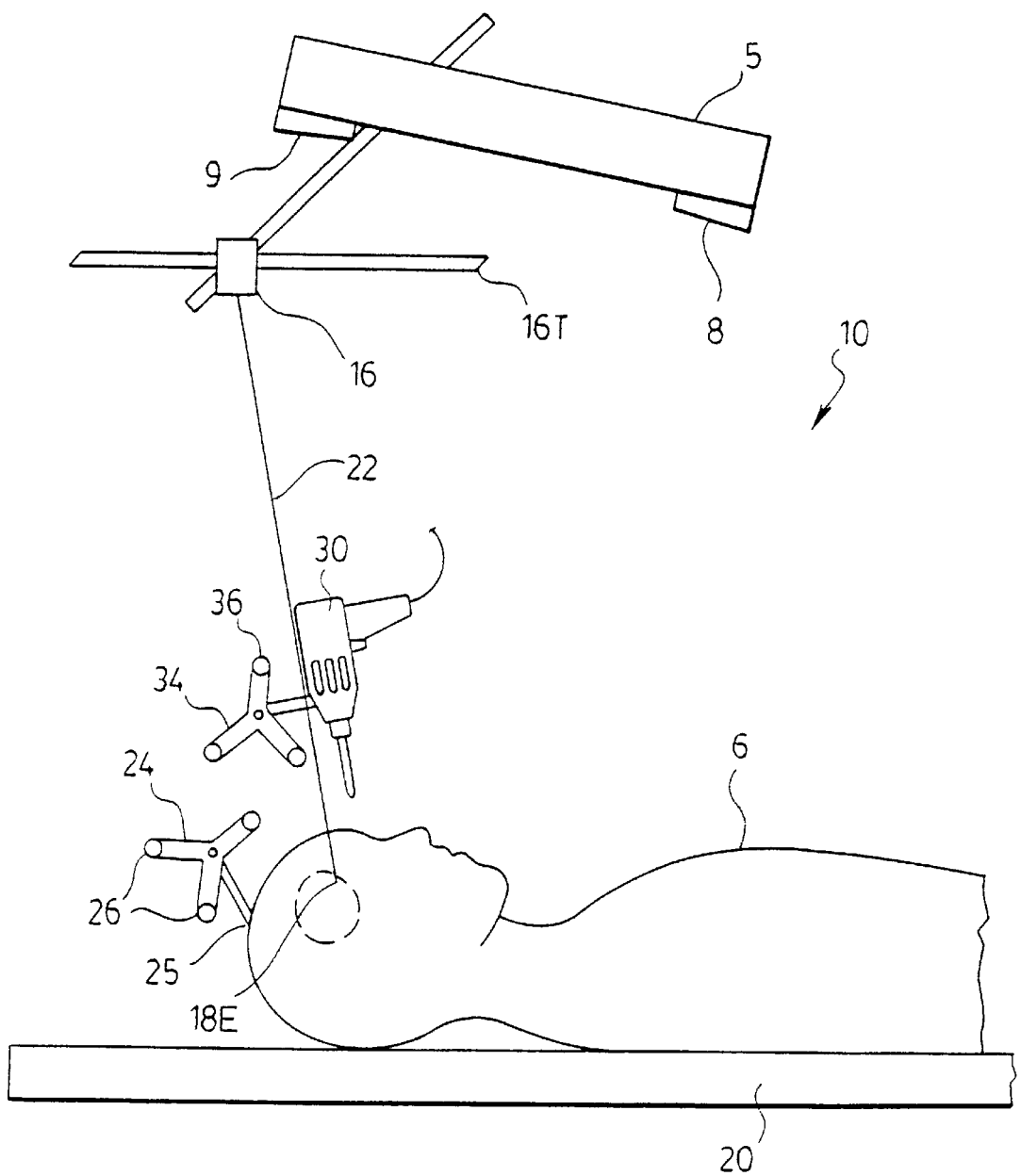
FIG. 3 is a symbolic representation of a system according to one embodiment of the present invention used to guide a drill.

FIG. 3 shows a further embodiment of the present invention. In FIG. 3, the image projecting device 16 is projecting the laser beam 22 at an entry point 18E into the patient 6.

It is apparent from a comparison of FIGS. 2 and 3 that the entry point 18E corresponds to a specific point on the image 18I shown in FIG. 2. In other words, in FIG. 2 the image projecting device 16 is projecting the image 18I of a first marking 18M made on the data-base body 13 which represents the portion of the skull of the patient 6 which is to be removed. In FIG. 3, the image projecting device 16 is projecting the image of the entry point 18E which corresponds to the markings 18M made on the data-base body 13 indicating the desired entry point to the patient 6 in order to remove the portion of the skull represented by image 18I. The projecting device 16 could either project the image 18I or the image of the entry point 18E according to the signals inputted from the input unit 12I as discussed above. Alternatively, both the image 18I and the image of the entry point 18E could be projected at the same time.

In the case of the entry point 18E, a surgeon may be concerned not only with the position of the entry point 18E, but also the orientation of the entry point 18E. The markings 18M on the data-base body 13 would likely include a vector having a position, as well as an orientation, to uniquely identify the entry point in six degrees of freedom. Accordingly, the image of the entry point 18E will have an orientation and position which corresponds to both the position and orientation of the markings 18M made on the database body 13.

As shown in FIG. 3, the orientation and position of the laser beam 22, which corresponds to the markings 18M made on the data-base body 13, can be used by the surgeon to align instruments, such as drill 30, for entry into the patient 6. It is apparent that as the surgeon aligns the drill 30 by means of the laser beam 22, the surgeon will have the benefit of seeing the image of the entry point 18E corresponding to the markings 18M made on the data-base body 13, as well as be able to observe the drill 30 as it cuts into the entry point 18E of the patient 6. In this way, the surgeon will not only know that the position of the drill 30 corresponds to the markings 18M made on the data-base body 13, but the surgeon will also be able to view the drill 30 entering into the entry point 18E. This will assist the surgeon in orienting the drill 30, as well as permit the surgeon to become immediately aware of any "critical structures" which may be encountered by the drill 30, even if these "critical structures" did not appear on the pre-acquired images 11.

The drill 30 may also be attached to a tracking tool 34, similar to the tracking tool 24 attached to the patient 6. The tracking tool 34 can comprise tracking elements 36 which are tracked by the cameras 8, 9 when the spatial determinator 5 comprises an optical tracking system. In this way, the drill 30 can also be tracked in the frame of reference 2 and a representation of the tool 30 may appear on the data-base body 13 of pre-acquired image 11. As such, the surgeon will have the benefit of both viewing the orientation and position of the markings 18M projected by the image projecting device 16 on the patient 6, as well as viewing a representation of the drill 30 on the data-base body 13 of pre-acquired images 11, as is done on conventional systems.

In a further preferred embodiment, the system 10 may generate an audible alarm if the position of the drill 30, as perceived by the cameras 8, 9 deviates from the orientation and position of the markings 18M as represented by the laser beam 22. In this way, the surgeon will be immediately advised if the drill 30 does not follow the path of the markings 18M made on the data-base body 13 of pre-acquired images 11.

Figure 4:
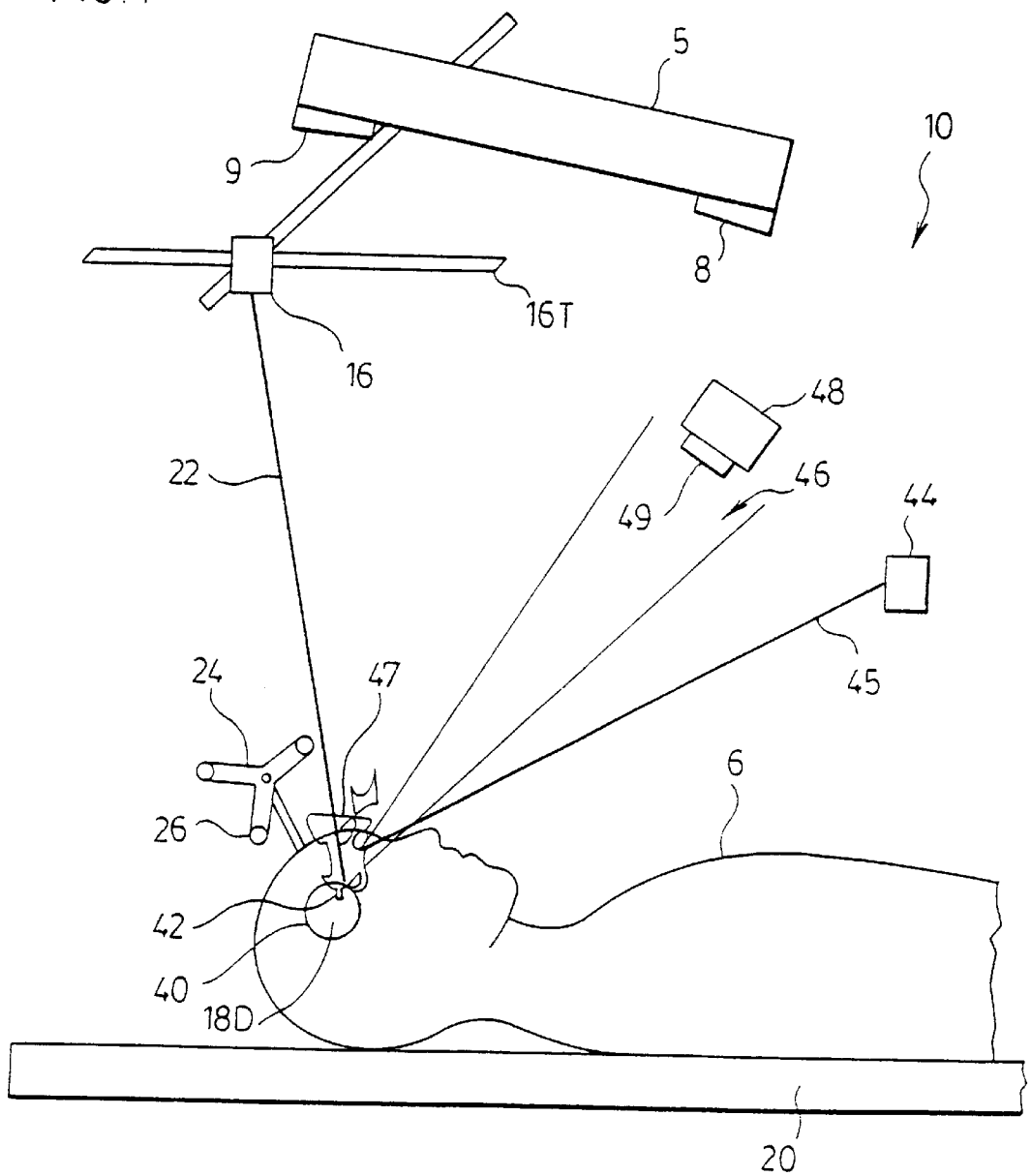
FIG. 4 is a symbolic representation of a system according to one embodiment of the present invention used to diagnose or treat a patient.

FIG. 4 shows a further embodiment of the present invention. In FIG. 4, a portion of the skull of the patient 6 has been removed. It will be apparent from a comparison of FIGS. 2 and 4 that the hole in the skull 40 corresponds to the image 18I made by the image projecting device 16 and illustrated in FIG. 2. Accordingly, the surgeon has removed a portion of the skull 40 as pre-planned and as projected by the image 18I onto the patient 6 as shown in FIG. 2.

With the portion of the skull removed, a treatment area 42 is revealed. In a preferred embodiment, the image projecting device 16 can also be used to diagnose and/or treat the patient 6 as follows.

As shown in FIG. 4, a radiation detecting device 48 is present to detect radiation from the anatomical body 6. The radiation detecting device 48 has a field of view 46 and will detect radiation reflected from the anatomical body 6, and more specifically the treatment area 42 of the anatomical body 6. In this way, the image projecting device 16 can project diagnostic images 18D, and if desired, with different types of radiation, into the treatment area 42 corresponding to markings 18M made on the data-base body 13. The radiation from the diagnostic image 18D will be reflected towards the field of view 46 of the radiation detecting device 48. By using different types of radiation, the radiation detecting device 48 will be able to analyze the radiation detected from the treatment area 42 of the anatomical body 6 to determine characteristics of the anatomical body 6 being radiated by the image projecting device 16. In this way, diagnostic procedures can be performed within the treatment area 42 based on diagnostic markings 18D previously made to the data-base body 13.

It is understood that the image detecting device 48 comprises a detector 49 which detects the radiation reflected from the anatomical body 6 in field of view 46. The radiation detecting device 48 also comprises the electronics to analyze the radiation detected from the anatomical body 6 to determine the characteristic of the anatomical body being irradiated. Rather than having the electronics located proximate the detector 49, the electronics can be located in another location, and could be contained within the computer 12. Also, while the detector 49 for the radiation detecting device 48 is shown separate from the spatial determinator 5, in one embodiment where the spatial determinator 5 comprises an optical tracking system, the cameras 8, 9 of the optical tracking system may also be used as the detector 49 for the radiation detecting device 48 if the cameras 8, 9 can detect the type of radiation being reflected from the anatomical body 6.

Also, as shown in FIG. 4, in addition to the image projecting device 16, a second separate beam source 44 which emits beam 45 could be used in addition to, or in replacement of, the image projecting device 16 and the beam 22. Of course, if the beam source 44 is to project an image 18D corresponding to the markings 18M made on the data-base body 13, it will be necessary for the beam source 44 to receive signals corresponding to the mapping signals $M_S$, as is done by the image projecting device 16.

In a further preferred embodiment, the system 10 can be used to treat the patient 6. This can be done in one manner by applying a substance to the anatomical body 6 which reacts to a specific type of radiation. Preferably, the reaction would cause cells of the anatomical body 6 to which the substance and radiation have been applied to change. For example, the substance can become cytotoxic and kill the cells in its vicinity in reaction to specific types of radiation. For example, the substance may comprise a photodynamic agent which is applied either to the surface of the treatment area 42, intravenously or orally by the patient 6. The photodynamic agent can be taken up non-preferentially by the healthy tissue, as well as any tumours, in the patient 6. The photodynamic agent can then react to the radiation from the laser beam 22 to change the cells of the anatomical body 6 such as by becoming cytotoxic and killing the cells in the vicinity.

Because the images 18D can be projected in a precise manner to irradiate objects in the treatment area 42, corresponding to markings 18M on the data-base body 13, more precise irradiation of the treatment area 42 can be accomplished. In this way, only the tumours within the treatment area 42 can be irradiated, thereby providing more precise photodynamic therapy. Also, because of the precision of the application of the radiation by means of the projecting device 16, more general photodynamic agents can be used which may be partially absorbed by the healthy tissue, as well as the tumour, because the laser beam 22 will only be directed to an image corresponding to the markings 18M on the tumour in the data-base body 13. For the same reasons, a more intense laser beam 22 could be used.

In a similar manner, an intense laser beam 22 can be used without a substance, such as a photodynamic agent, to treat the patient 6. For example, if a tumour bed has been marked on the data-base body 13, an intense beam, such as from a $CO_2$ laser, can be used to cauterize the tumour bed. In this way, the tumour bed, or other portion of the anatomical body 6, can be cauterized in a rapid and precise manner.

It is understood that the image detecting device 48 comprises a detector 49 that detects the radiation reflected or emitted by means of a photonic interaction from the anatomical body 6 or a debris plume 47. The second beam source 44, and if desired, a third beam source (not shown) could be used to induce a photonic reaction in the plume 47, including non-linear optical effects, Raman or fluorescent scattering or similar effects to determine partial or complete composition of the plume 47 or components thereof. Using the well-known principle of "differential absorption", it is possible to determine the chemical composition of the plume 47 by comparing the relative absorption of two closely tuned laser beams 22, 45.

In addition, the system 10 can be used in other procedures in order to treat the patient 6. For example, tattoos or other surface blemishes may appear on pre-acquired images 11. The tattoos can be marked by markings 18M on the data-base body 13 formed by the pre-acquired images 11. The image projecting device 16 can then emit radiation which will blanch the tattoos or other surface blemishes in a rapid and precise manner corresponding to markings 18 made on the database body 13.

Figure 6A:
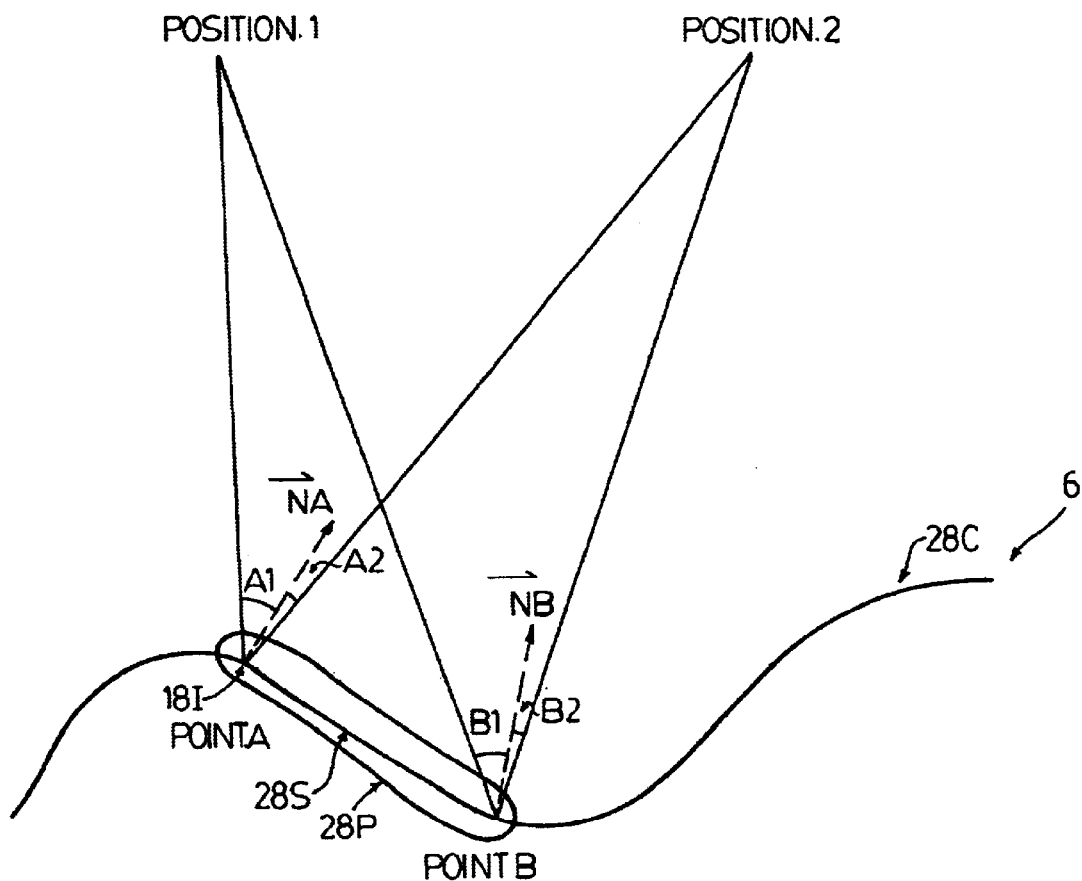
FIG. 6A illustrates the projection of an image onto the anatomical body from an image projecting device at two different positions.

As described above, in order to improve the precision and accuracy of the image 18I, and decrease optical distortions, it is preferred that the image projecting device 16 project the image 18I substantially normal to a surface 28S where at least a portion 28P of the corresponding locations 28C are located on the anatomical body 6. This is illustrated in FIG. 6A which shows the image 18I projected at two different points, namely Point A and Point B. FIG. 6A shows the normals NA and NB to the surface 28S at two points, namely Point A and Point B. When the image projecting device 16 is at position 1, there are large angles A1, B1 with respect to the normals NA, NB at points A and B. These angles A1, B1 are generally larger than about 30 degrees with the normal NA, NB. Because of this, the image projected at Point A will have optical distortion errors, as illustrated by the oval identified by reference numeral 180E in FIG. 6B. However, if the image projecting device 16 is at position 2, the image 18I would be substantially normal to the surface 28S of the portion 28P of the corresponding locations 28C of the anatomical body 6 and there would be smaller angles $A_2$, $B_2$ with respect to the normals NA, NB at Points A, B. Because of this, the image 18I projected at Point A, as well as Point B, would be much more precise, as illustrated by the dot identified by reference numeral 180P in FIG. 6C.

If the image 18I is produced by rapidly scanning a coherent beam of light over the portion 28P of the corresponding locations, then it is clear that having the smaller angles $A_2$, $B_2$ with respect to the normals NA, NB will produce a more accurate and clearer image 18I. Furthermore, if the image 18I is produced by projecting a fixed image, such as a slide or computer generated image, then preferably the angle of incidence of the image 18I is substantially normal to the surface 28S of at least a portion of the corresponding locations.

Accordingly, FIGS. 6A, 6B and 6C illustrate that projecting the image 18I substantially normal to the surface 28S of a portion 28P of the corresponding locations 28C of the anatomical body 6 decrease the optical distortion errors and improves precision and accuracy of the image 18I. To accomplish this, the image projecting device 16 is preferably oriented with respect to the anatomical body 6 such that the image 18I projected by the image projecting device 16 forms an angle within about 45 degrees, and more preferably about 30 degrees, with the normal NA, NB of the surface 28S of the portion 28P of the corresponding locations 28C.

As described above, in order to orient the image projecting device 16, the system 10 preferably comprises a translation device 16T. The translation device 16T can move the image projecting device 16 within the frame of reference 2. Furthermore, the image projecting device 16 and the translating device 16T comprise mirrors (not shown) which can change the position and orientation of the image being projected by the image projecting device 16. In the embodiment where the image projecting device 16 comprises an emitter of coherent light, such as a laser, the image projecting device 16 may also comprise mirrors (not shown) having a range of either 20 degrees or 40 degrees, for example, to change the orientation and/or position of the emitted coherent beam of light.

However, in some cases, the orientation and/or position of the emitted beam of light from the image projecting device 16 must be altered more than this amount. Accordingly, in a preferred embodiment, the translation device 16T comprises a swivel/tilt base unit 160, as shown in FIG. 7. The swivel/tilt base unit 160 comprises a pan rotary table 162 and a tilt rotary table 164 which permit the image projection device 16 to be oriented over a larger range of positions and orientations. As illustrated in FIG. 7, a tracking device 54 is attached to the image projecting device 16 in order to track its position and orientation in the frame of reference 2.

In the event that the corresponding location 28C is too large so that the image 18I can be projected substantially normal to the entire surface 28S, it is preferred that the image 18I be separated into two portions, namely the first portion $18I_1$ and the second portion $18I_2$. The first portion $18I_1$ will be known to be projected substantially normal to the surface 28S of the portion 28P of the corresponding locations 28C. The second portion $18I_2$ will be known not to be substantially normal to the surface 28S of the portion 28P of the corresponding locations 28C. In order to indicate this to the surgeon, thereby advising the surgeon of the potential errors inherent in the second image $18I_2$, the second image $18I_2$ is projected in a manner perceptively different from the manner in which the first image $18I_1$ is projected, as shown in FIG. 7. For instance, the first image $18I_1$ may be projected in solid lines and the second image $18I_2$ may be projected in dashed lines. Alternatively, different wavelengths, and therefore colours, could be used for the first image $18I_1$ and the second image $18I_2$.

In order to have more of the image 18I substantially perpendicular to the surface 28S of the portion 28P of the corresponding location 28C, the image projecting device 16 may have more than one emitter. For example, as shown in FIG. 5, the system 10 may have an image projecting device 16 with a second emitter 16S which can be moved by the translation device 16T to a position and orientation to project an image 18I, such as by emitting visible light, substantially normal to a surface 28S of another portion of the corresponding locations 28C. If the two emitters emit light having the same wavelength, the fact that there are two separate emitters may not even be apparent to the surgeon. For any portion of the image 18I which still cannot be projected normal to a surface 28S, two perceptively different manners of projecting the non-normal image can be used, as described above.

It understood that while the present invention has been described in terms of the anatomical body 6 of the human, the system 10 and method of using the system 10 are not limited to use on humans. Rather, the system 10 and method of using the system 10 can be used in veterinary and other applications where an image of markings made on pre-acquired images 11 must be projected onto the corresponding locations of the objects from which the images were acquired.

It is also understood that while the present invention has been described and illustrated in terms of a surgical procedure on the skull of the patient 6, the invention is not limited to this application. Rather, the invention can be used in any type of surgical procedure where projection of images corresponding to the markings 18M made on pre-acquired images 11 will facilitate image guided surgery.

It is understood that while the present invention has been described and illustrated in terms of certain types of translation devices 16T for moving the image projecting device 16 to a position and orientation such that the image projecting device 16 projects the image 18 substantially normal to the surface 28S of a portion 28P of the corresponding locations, the invention is not limited to these specific types of translation devices 16T. Rather, the present invention includes all types of devices which can perform the function of moving the image projecting device 16 to a position and orientation such that the image projecting device 16 projects the image 18 substantially normal to the surface 28S of a portion 28P of the corresponding locations. Without limiting the foregoing, this would include robots or robot arms which can move the image projecting device 16 in the frame of reference 2.

It is also understood that while the invention has been described in some embodiments as comprising a coherent beam of light, this invention is not limited to coherent beams of light, but rather could comprise other beams of light, such as collimated beams of light.

It will be understood that, although various features of the invention have been described with respect to one or another of the embodiments of the invention, the various features and embodiments of the invention may be combined or used in conjunction with other features and embodiments of the invention as described and illustrated herein.

Although this disclosure has described and illustrated certain preferred embodiments of the invention, it is to be understood that the invention is not restricted to these particular embodiments. Rather, the invention includes all embodiments which are functional, electrical or mechanical equivalents of the specific embodiments and features that have been described and illustrated herein.

What is claim is:

1. A system far projecting onto an anatomical body markings made on a data-base body of pre-acquired images of the anatomical body, said system comprising:
    a spatial determinator for determining spatial positional information of the anatomical body by tracking the anatomical body in a frame of reference and generating first positional signals indicative of the spatial positional information of the anatomical body in the frame of reference;
    a mapping unit for receiving first positional signals indicative of the spatial positional information of the anatomical body in the frame of reference, mapping the markings made on the data-base body of pre-acquired images onto corresponding locations on the anatomical body and generating a mapping signal indicative of the corresponding locations in the frame of reference of the markings on the data-base body; and
    an image projecting device for receiving the mapping signal and projecting an image of the markings made on the data-base body onto the corresponding locations of the anatomical body, said image projecting device projecting the image at an angle within about 30 degrees of the normal of a surface of a portion of the corresponding locations of the anatomical body.

2. The system as defined in claim 1 wherein the image projecting device projects the image substantially normal to the surface of the portion of the corresponding locations by projecting the image substantially normal to the surface of the portion of the corresponding locations.

3. The system as defined in claim 1 wherein the image projecting device emits a coherent beam of light; and
    wherein the image projecting device is oriented with respect to the anatomical body such that the coherent beam of light is within about 30 degrees of the normal of the surface of the portion of the corresponding locations.

4. The system as defined in claim 3 wherein the normal of the surface of the corresponding locations of the anatomical body are calculated from the pre-acquired images.

5. The system as defined in claim 4 wherein the normal of the surface of the corresponding locations of the anatomical body calculated from the pre-acquired images are confirmed by the image projecting device projecting known images on the portion of the surface of the anatomical body and monitoring the known images to determine if the projected known images appear in a manner consistent with the calculated normals.

6. The system as defined in claim 3 wherein a first portion of the image is projected substantially normal to the surface of the portion of the corresponding locations and a second portion of the image is projected other than substantially normal to the surface of the portion of the anatomical body; and
    wherein the first portion of the image is projected in a first manner and the second portion of the image is projected in a second manner perceptively different from the first manner.

7. The system as defined in claim 6 the image projecting device emits a first coherent beam of visible light having a first wavelength and a second beam of coherent light having a second wavelength perceptively different from the first wavelength; and
    wherein the first portion of the image is projected in the first wavelength and the second portion of the image is projected in the second wavelength.

8. The system as defined in claim 3 wherein the image projecting device emits a first coherent beam of visible light having a first wavelength and a second coherent beam of visible light having a second wavelength different from the first wavelength; and
    wherein the information inputted into the input unit selects which markings made on the data-base body are projected by the first coherent beam of visible light and the second coherent beam of visible light.

9. The system as defined in claim 1 further comprising translation devices for moving the image projecting device in response to a translation signal to a position and orientation such that the image projecting device projects the image within 30 degrees of the normal to the surface of the portion of the corresponding locations.

10. The system as defined in claim 9 wherein the spatial determinator tracks the position and orientation of the image projecting device in the frame of reference and generates image projecting position signals indicative of the position of the image projecting device in the frame of reference; and
    wherein the mapping unit receives the image projecting position signals, and sends the translation signal to the translation device to move the image projecting device to a position and orientation with respect to the anatomical body such that the image projecting device projects the image substantially normal to the surface of the portion of the corresponding locations.

11. The system as defined in claim 10 wherein the spatial determinator comprises an optical tracking system to track objects in the frame of reference; and
    wherein the optical tracking system optically tracks the anatomical body in the frame of reference and generates the first positional signals indicative of the spatial positional information of the anatomical body in the frame of reference.

12. The system as defined in claim 11 wherein the image projected by the image projecting device can be tracked by the optical tracking system; and
    wherein the optical tracking system tracks the image projected by the image projecting device and generates second positional signals indicative of the spatial positional information of the image in the frame of reference; and
    wherein the mapping unit receives the first positional signals and second positional signals and determines whether the image being projected by the image projecting device corresponds to the markings made on the data-base body of pre-acquired images.

13. The system as defined in claim 12 wherein if the mapping unit determines that the image being projected by the image projecting device does not correspond to the markings made on the data-base body, the mapping unit regenerates the mapping signal to cause the projecting device to project a more accurate image of the markings made on the data-base body.

14. The system as defined in claim 11 wherein the optical tracking system is proximate the image projecting device in The frame of reference.

15. The system as defined in claim 14 wherein the translation devices move the optical tracking system with the image projecting device, such that the image projecting position signals correspond to a position of the optical tracking system in the frame of reference.

16. The system as defined in claim 14 further comprising a first optical tracker fixed to the anatomical body and a second optical tracker fixed to the image projecting device; and wherein the optical tracking system tracks the anatomical body in the frame of reference by tracking the first and second optical trackers.

17. The system as defined in claim 9 wherein the image projecting device comprises a first coherent beam of light emitter for emitting visible light having a first wavelength and a second coherent light emitter for emitting visible light having a second wavelength wherein the translation devices can move the first emitter with respect to the second emitter.

18. The system as defined in claim 17 wherein the translation devices move the first emitter to a position and orientation to emit visible light substantially normal to the surface of the portion of the corresponding location and the second translation devices move the second emitter to a position and orientation to emit visible light substantially normal to a surface of another portion of the corresponding locations.

19. The system as defined in claim 1 wherein the image projecting device emits a coherent beam of light which can mark the anatomical body such that the image of the markings projected by the image projecting device will appear on the anatomical body after the image projecting device ceases projecting the image.

20. The system as defined in claim 1 further comprising:
a substance which reacts to a type of radiation by changing in a perceptible manner;
wherein the image projecting device emits the type of radiation to which the substance reacts; and
wherein the substance can be applied to the anatomical body such that projecting the image in the type of radiation to which the substance reacts onto the anatomical body will mark the anatomical body with the image projected by the image projecting device.

21. The system as defined in claim 1 further comprising:
a marking material having embedded therein a substance which reacts to a type of radiation by changing in a perceptible manner;
wherein the image projecting device emits the type of radiation to which the substance reacts; and
wherein the marking material can be applied to the anatomical body such that projecting the image in the type of radiation to which the substance reacts onto the marking material will mark the marking material on the anatomical body with the image projected by the image projecting device.

22. The system as defined in claim 21 wherein the type of radiation is selected from the group consisting of infrared radiation, ultraviolet radiation, x-ray radiation and particle beams.

23. The system as defined in claim 1 further comprising:
a substance which reacts to a specific type of radiation by changing cells of the anatomical body to which the substance has been applied; and
wherein projecting the image in the type of radiation to which the substance reacts onto the anatomical body changes the cells of a portion of the anatomical body to which the substance is applied and the type of radiation is projected.

24. The system as defined in claim 1 further comprising:
radiation detecting device for detecting radiation from the anatomical body;
wherein the image projecting device projects the image of the markings made on the data-base body onto the corresponding locations of the anatomical body using types of radiation which can be reflected from the anatomical body towards the radiation detecting device; and
wherein the radiation detecting device analyzes the radiation detected from the anatomical body to determine a characteristic of the anatomical body being irradiated by the image projecting device.

25. The system as defined in claim 24 wherein the spatial determinator comprises an optical tracking system to track objects in the frame of reference;
wherein the optical tracking system optically tracks the anatomical body in the frame of reference and generates the first positional signals indicative of the spatial positional information of the anatomical body in the frame of reference; and
wherein the optical tracking system and the radiation detecting device share a common radiation detector.

26. The system as defined in claim 1 further comprising:
a storage unit for storing said data-base body of pre-acquired images, said storage unit being connected to the mapping unit;
an input unit connected to said storage unit for inputting information, said information comprising markings made onto the data-base body of pre-acquired images;
wherein information corresponding to markings made on the data-base body of pre-acquired images can be inputted at all times; and
wherein the image projected by the image projecting device can comprise the markings made on the data-base body by information inputted through the input unit.

27. A method for projecting onto an anatomical body markings made on a data-base body of pre-acquired images of the anatomical body, said method comprising the steps of:
obtaining spatial positional information of the anatomical body by tracking the anatomical body in a frame of reference;
mapping the markings made on the data-base body of pre-acquired images onto corresponding locations on the anatomical body; and
projecting an image of the markings made on the data-base body onto the corresponding locations on the anatomical body in the frame of reference at an angel within about 30 degrees of the normal of a surface of a portion of the corresponding locations of the anatomical body.

28. The method as defined in claim 27 further comprising the steps of projecting the image with an image projecting device; and marking the anatomical body with the image projected by the image projecting device such that the image projected by the image projecting device will appear on the anatomical body after the image projecting device ceases projecting the image.

29. The method as defined in claim 27 wherein the image projecting device projects the image substantially normal to the surface of the portion of the corresponding locations.

30. The method as defined in claim 29 further comprising the steps of:

projecting a first portion of the image in a first manner and projecting a second portion of the image in a second manner perceptively different from the first manner; and wherein the first portion of the image is projected within about 30 degrees of the normal of the surface of the corresponding locations and the second portion of the image is not within about 30 degrees of the normal of the surface of the corresponding locations.

31. The method as defined in claim 27 further comprising the steps of:

projecting the image with an image projecting device which emits a coherent beam of light; and orienting the image projecting device with respect to the anatomical body such that the coherent beam of light is substantially normal to the surface of the portion of the corresponding locations.

32. The method as defined in claim 27 further comprising the preliminary steps of:

(a) calculating the normal of the surface of the corresponding locations from the pre-acquired images; and (b) confirming the calculated normals of the surface of the corresponding locations by
 (i) projecting known images on the surface of the corresponding locations; and
 (ii) monitoring the known images to determine if the projected known images appear in a manner consistent with the calculated normals.

33. The method as defined in claim 27 further comprising the steps of:

projecting the image with an image projecting device;

determining the position and orientation of the image projecting device in the frame of reference; and moving the image projecting device to a position and orientation such that the image projecting device projects the image substantially normal to the surface of the position of the corresponding locations.

34. The method as defined in claim 27 further comprising the step of:

temporarily marking the anatomical body with the image projected by an image projecting device.

35. The method as defined in claim 34 further comprising the steps of:

applying a substance to the anatomical body which reacts to a specific type of radiation by changing in a perceptible manner; and projecting the type of radiation to which the substance reacts onto the anatomical body corresponding to the markings made to the data-base body of pre-acquired images so that the anatomical body is temporarily marked with the image projected by the image projecting device.

36. The method as defined in claim 27 further comprising the steps of:

applying a substance to the anatomical body which reacts to a specific type of radiation by changing cells of the anatomical body w which the substance has been applied; and wherein projecting the image in the type of radiation to which the substance reacts onto the anatomical body changes the cells of a portion of the anatomical body to which the substance is applied and the type of radiation is projected.

37. The method as defined in claim 27 wherein the step of projecting an image of the markings onto the anatomical body comprises the step of projecting a visible image of the markings onto the anatomical body.

38. The method as defined in claim 27 further comprising an image projecting device which emits a first coherent beam of visible light; and wherein the step of projecting an image of the markings onto the anatomical body comprises the step of projecting a visible beam of light having a position and orientation corresponding to the markings made on the data-base body.

39. The method as defined in claim 38 wherein the image projecting device emits a second coherent beam of visible light at a different wavelength from the first coherent beam of visible light; and wherein the first and second coherent beams of visible light project images of different markings onto the anatomical body corresponding to the markings made on the data-base body of pre-acquired images.

* * * * *